United States Patent
Theeuwes et al.

(10) Patent No.: US 6,872,201 B2
(45) Date of Patent: Mar. 29, 2005

(54) OSMOTIC DELIVERY SYSTEM HAVING SPACE EFFICIENT PISTON

(76) Inventors: Felix Theeuwes, 27350 Altamont Rd., Los Altos Hills, CA (US) 94022; Ben Eckenhoff, deceased, late of Los Altos, CA (US); by Bonnie Burdett Dennis, legal representative, 1080 Autumn La., Los Altos, CA (US) 94024

( * ) Notice: Subject to any disclaimer, the term of this patent is extended or adjusted under 35 U.S.C. 154(b) by 0 days.

(21) Appl. No.: 10/354,142

(22) Filed: Jan. 30, 2003

(65) Prior Publication Data

US 2003/0139732 A1 Jul. 24, 2003

Related U.S. Application Data

(63) Continuation of application No. 09/472,600, filed on Dec. 27, 1999, now Pat. No. 6,544,252.
(60) Provisional application No. 60/114,548, filed on Dec. 31, 1998.

(51) Int. Cl.[7] ............................ A61K 9/22; A61K 13/00
(52) U.S. Cl. ..................................... 604/892.1; 424/422
(58) Field of Search ........................... 604/890.1, 891.1, 604/892.1, 130–133, 141, 143, 151, 218; 424/422, 451, 452, 464, 465

(56) References Cited

U.S. PATENT DOCUMENTS

| | | | |
|---|---|---|---|
| 3,732,865 A | 5/1973 | Higuchi et al. | |
| 3,995,632 A | 12/1976 | Nakano et al. | |
| 4,619,652 A | 10/1986 | Eckenhoff et al. | |
| 4,874,388 A | 10/1989 | Wong et al. | |
| 5,062,841 A | 11/1991 | Siegel | |
| 5,221,278 A | 6/1993 | Linkwitz et al. | |
| 5,234,424 A | 8/1993 | Yum et al. | |
| 5,279,608 A | 1/1994 | Cherif Cheikh | |
| 5,318,558 A | 6/1994 | Linkwitz et al. | |
| 5,639,477 A | 6/1997 | Maruyama et al. | |
| 5,997,527 A | 12/1999 | Gumucio et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,544,252 B1 * | 4/2003 | Theeuwes et al. ....... | 604/892.1 |

FOREIGN PATENT DOCUMENTS

GB      2178659 A     2/1987

OTHER PUBLICATIONS

U.S. patent application No. 08/595,761.
F. Theeuwes et al., "Principles of the Design and Operation of Generic Osmotic Pumps for the Delivery of Semisolid or Liquid Drug Formulation", Annals of Biomedical Engineering 4 (1970), pp 343–353.

* cited by examiner

Primary Examiner—Sharon Kennedy

(57) ABSTRACT

An osmotic delivery system having a space-efficient piston is provided. The enclosure has an interior holding the position, a beneficial agent, and an osmotic agent including a tablet. The piston is movable with respect to an interior surface of the capsule, and defines a movable seal with the interior surface of the capsule. The movable seal separates the osmotic agent from the beneficial agent. The piston has a recess that receives at least a portion of the osmotic agent. The osmotic agent imbibes liquid from a surrounding environment through a semipermeable body to cause the piston to move and in turn cause delivery of the beneficial agent from the capsule.

22 Claims, 4 Drawing Sheets

OSMOTIC DELIVERY SYSTEM HAVING SPACE EFFICIENT PISTON

CROSS-REFERENCE TO RELATED APPLICATIONS

The present invention is a continuation of, and claims priority from U.S. patent application Ser. No. 09/472,600, filed Dec. 27, 1999, now U.S. Pat. No. 6,544,252, issued Apr. 8, 2003, which claims the benefit of U.S. Provisional Application Ser. No. 60/114,548, filed on Dec. 31, 1998, the entire disclosures of which are hereby incorporated herein by reference in their entireties.

BACKGROUND OF THE INVENTION

1. Field of the Invention

The present invention relates to osmotic delivery systems for delivering beneficial agents, and more particularly, to an osmotic delivery system having a piston with a recess for receiving an osmotic agent.

2. Description of the Related Art

Controlled delivery of beneficial agents, such as drugs, in the medical and veterinary fields, has been accomplished by a variety of methods. One method for controlled prolonged delivery of beneficial agents involves the use of osmotic delivery systems. These devices can be implanted to release beneficial agents in a controlled manner over a preselected time or administration period. In general, osmotic delivery systems operate by imbibing liquid from the outside environment and releasing corresponding amounts of the beneficial agent.

A known osmotic delivery system, commonly referred to as an "osmotic pump," generally includes some type of capsule or enclosure having a semipermeable portion that may selectively pass water into an interior of the capsule that contains a water-attracting osmotic agent. In such a known osmotic delivery system, the walls of the capsule are substantially impermeable to items within and outside the capsule, and a plug acts as the semipermeable portion. The difference in osmolarity between the water-attracting agent and the exterior of the capsule causes water to pass through the semipermeable portion of the capsule, which in turn causes the beneficial agent to be delivered from the capsule through the delivery port. The water-attracting agent may be the beneficial agent delivered to the patient. However, in most cases, a separate osmotic agent is used specifically for its ability to draw water into the capsule.

In some instances, a piston is required to separate the beneficial agent from the osmotic agent to prevent the osmotic agent from mixing with or contaminating the beneficial agent. The structure of the capsule is such that the capsule does not expand when the osmotic agent takes in water and expands. As the osmotic agent expands, pressure causes the piston to move and the beneficial agent to be discharged through the delivery orifice at the same rate as the liquid, which is typically water, enters the osmotic agent by osmosis. Osmotic delivery systems may be designed to deliver a beneficial agent at a controlled constant rate, a varying rate, or in a pulsatile manner.

In those osmotic delivery systems that require the use of a piston to separate the beneficial agent and the osmotic agent, the piston necessarily occupies space in the capsule. Hence, if the piston is needed to separate the beneficial agent and the osmotic agent, and the size of the capsule is not changed, the amount of beneficial agent or osmotic agent that can be held within the capsule decreases as compared to another osmotic delivery system having the same size capsule that does not include a piston. Decreasing the amount of beneficial agent within the capsule detrimentally decreases the net amount of beneficial agent that can be delivered over a sustained period of time. Decreasing the amount of osmotic agent within the capsule detrimentally decreases the sustained period of time through which continuous delivery of the beneficial agent can be obtained.

But if the specific application requires a specific amount of beneficial agent or osmotic agent that cannot be varied and a piston must be used to separate the beneficial agent from the osmotic agent, the size of the capsule must be increased to accommodate for the extra space occupied by the piston such that the amount of osmotic agent or beneficial agent in the capsule does not vary. While simply increasing the size or volume of the capsule to accommodate for the extra volume occupied by the piston may appear to be a simple solution, because many osmotic delivery systems are destined for implantation in humans or animals, it is especially desirable to decrease the size of the osmotic delivery system as much as possible, while still allowing the osmotic delivery system to deliver the beneficial agent over a prolonged period of time. Additionally, simply increasing the size of the capsule for those applications requiring a piston that separates the beneficial agent from the osmotic agent is inexpedient as it is desirable to use one capsule for multiple osmotic delivery system applications. Moreover, it has been particularly problematic to increase the amount of time over which steady state release of the beneficial agent may be obtained with current osmotic delivery systems incorporating conventional pistons, without increasing the size of the capsule to hold more beneficial agent or osmotic agent. These problems associated with current osmotic delivery systems having known pistons have created a need for a solution.

SUMMARY OF THE INVENTION

Generally speaking, the present invention provides an osmotic delivery system that strives to efficiently utilize the space within the enclosure of the osmotic delivery system.

The present invention strives to address the disadvantages of known osmotic delivery systems by providing an osmotic delivery system having a capsule. The capsule has an interior for holding a beneficial agent. The. interior has an interior surface. An osmotic agent is located in the interior of the capsule. A semipermeable body is in liquid communication with the capsule and permits liquid to permeate through the semipermeable body to the osmotic agent. A piston is located within the interior of the liquid impermeable capsule. The piston is movable with respect to the interior surface of the capsule, and defines a movable seal with the interior surface of the capsule. The movable seal defined by the piston separates the osmotic agent from the beneficial agent. The piston has a recess that receives at least a portion of the osmotic agent. The osmotic agent is located between the piston and the semipermeable body. The osmotic agent imbibes liquid from a surrounding environment through the semipermeable body to cause the piston to move and in turn cause delivery of the beneficial agent from the capsule.

In accordance with another aspect of the present invention an osmotic delivery system includes a piston having a recess. An osmotic agent is located within the recess. An enclosure has an interior that holds the piston and the osmotic agent. The piston is movable with respect to the enclosure. The enclosure has a semipermeable body in liquid communication with the osmotic agent that permits liquid to permeate through the semipermeable body to the osmotic agent. The osmotic agent imbibes liquid from a surrounding environment and causes the piston to move.

According to another aspect of the present invention, an osmotic delivery system includes a capsule having a tubular interior. A semipermeable body is located at least partially within the tubular interior. A piston is located within the tubular interior. The piston has a recess. The piston defines a seal with an interior surface of the tubular interior. The piston is movable with respect to the interior surface of the tubular interior and with respect to the semipermeable body. An osmotic agent is located at least partially in the recess and the tubular interior. A beneficial agent is located within the tubular interior. The piston separates the beneficial agent from the osmotic agent. The semipermeable body is located on the same side of the liquid impermeable piston as the osmotic agent.

Other objects, advantages and features associated with the present invention will become readily apparent to those skilled in the art from the following detailed description. As will be realized, the invention is capable of other and different embodiments, and its several details are capable of modification in various obvious aspects, all without departing from the invention. Accordingly, the drawings and the description are to be regarded as illustrative in nature, and not limiting.

BRIEF DESCRIPTION OF THE DRAWINGS

The invention will be described in greater detail with reference to the accompanying drawings in which like elements bear like reference numerals, and wherein.

DETAILED DESCRIPTION OF THE INVENTION

Figure 1:
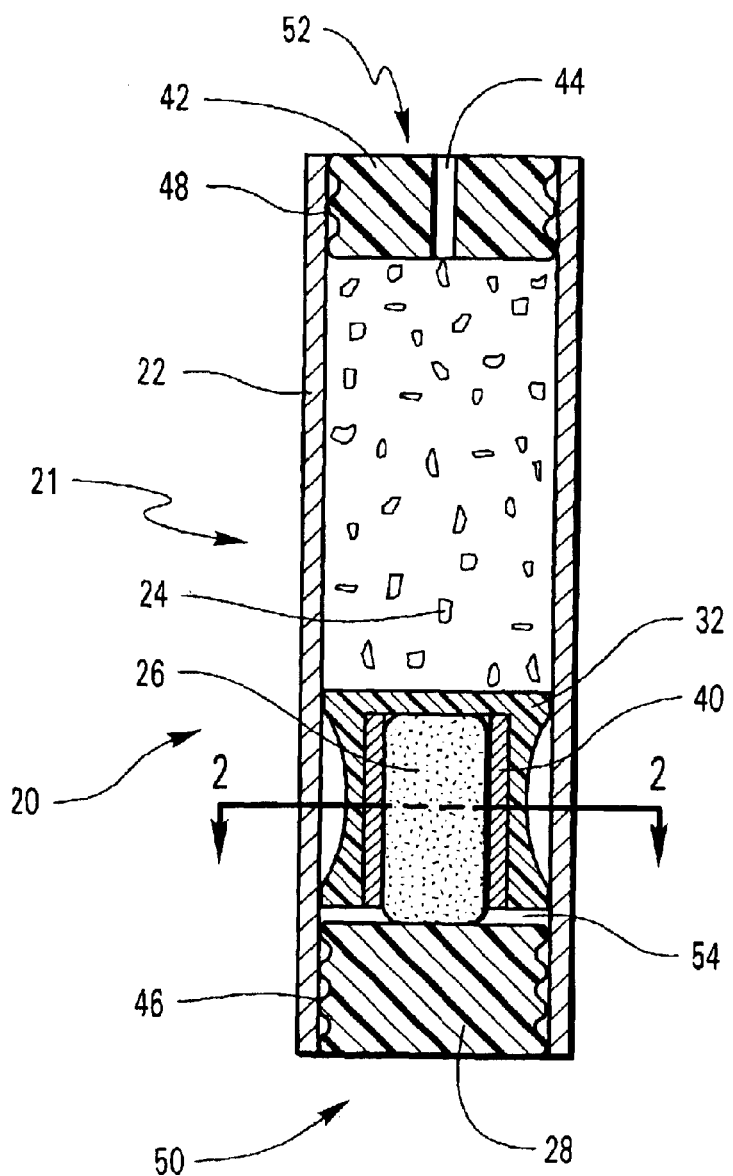
FIG. 1 is a sectional view of an osmotic delivery system according to one embodiment of the present invention.
Figure 2:
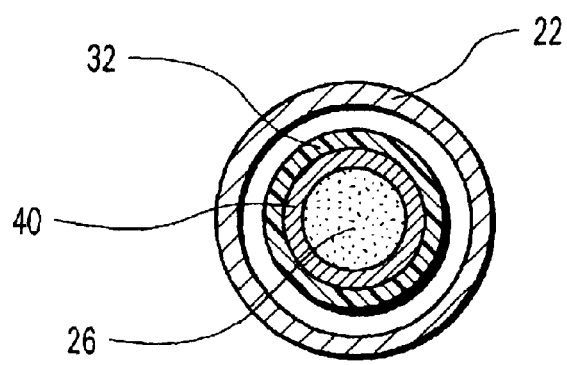
FIG. 2 is a sectional view of an osmotic delivery system according to the present invention taken along the line 2—2 of FIG. 1.

As shown in FIGS. 1–4, the present invention relates to an osmotic delivery system 20 for delivering a beneficial agent 24. The osmotic delivery system 20 includes a "space-efficient" piston 30. The piston 30 includes a recess 34 that receives an osmotic agent 26. The osmotic delivery system 20 also includes an enclosure 21 that encloses the piston 30 and the osmotic agent 26. The piston 30 is movable within the enclosure 21 and defines a movable seal that substantially prevents the osmotic agent 26 and the beneficial agent 24 from adversely affecting one another. A semipermeable body 28 is in liquid communication with the osmotic agent 26 and permits liquid to permeate through the semipermeable body to the osmotic agent. The osmotic agent 26 imbibes the liquid from a surrounding environment and causes the piston 30 to move, which, in turn, causes the beneficial agent 24 to be released from the osmotic delivery system 20.

The configuration of the osmotic delivery system 20 according to the present invention illustrated in FIGS. 1–4 is one example of an osmotic delivery device and is not to be construed as limiting the present invention. The present invention is generally applicable to all osmotic delivery devices having any number of shapes, and to all such devices administered in any variety of methods, such as oral, ruminal, and implantable osmotic delivery techniques. Such devices may also be placed in reservoirs, tanks, or pools.

Figure 3:
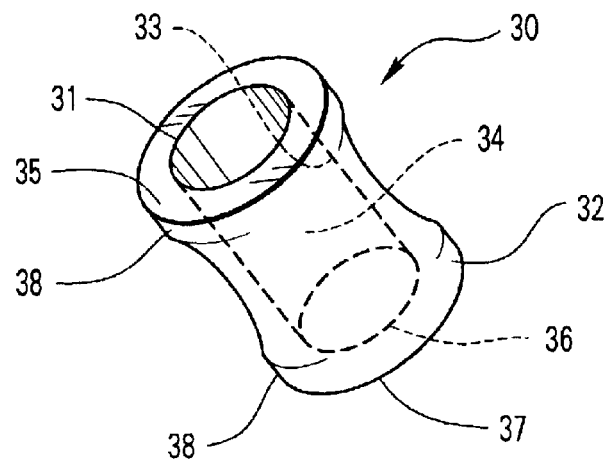
FIG. 3 is a perspective view of a piston according to one embodiment of the present invention.

The enclosure 21 of the osmotic delivery system 20 encloses or contains the osmotic agent 26 and the body 32 of the piston 30 (shown in FIG. 3). The enclosure 21 includes a tubular or elongated and substantially cylindrical capsule 22 illustrated in FIGS. 1 and 4. The capsule 22 has a first opening 51 at a first end 50 and a second opening 53 at a second end 52 opposite the first end 50. The enclosure 21 also includes the semipermeable body 28 that obstructs, blocks, closes-off, or plugs the first opening 51 in the capsule 22 to enclose the osmotic agent 26 and body 32 of piston 30. Thus, the first opening 51 receives the semipermeable body 28.

The enclosure 21 also includes a delivery port 44 located at the second end 52 of the capsule 22. The delivery port 44 delivers the beneficial agent 24 from the osmotic delivery system 20. According to other embodiments of the present invention, the capsule 22 may take different forms and shapes. For example, the capsule 22 can be tablet-shaped, have an elliptical cross-section, and can be formed from multiple piece tubes or cylinders, or two spheroidal sections. Additionally, the second opening 53 of the capsule 22 can define the delivery port 44, and the first opening 51 can define a channel for communicating a liquid, such as water, from a semipermeable body external of the capsule to an osmotic agent within the capsule. The first opening 51 can also define a channel for communicating a liquid from an external environment to a semipermeable body within the capsule.

The delivery port 44 is an orifice formed by conventional techniques. Included among these methods are mechanical drilling, laser drilling, and molding. The enclosure 21 will contain at least one such delivery port 44, and in most configurations, one delivery port will suffice. However, two or more delivery ports 44 may be present without departing from the present invention. The delivery port 44 may be formed in the capsule 22 itself, such as in the embodiment illustrated in FIG. 5 (shown as 144 and 122 respectively), or may be formed in a separate and distinct plug-like member 42 having means for sealing or ribs 48 extending outwardly from the outer surface thereof for insertion into the second opening 53 of the capsule 22. The delivery port 44 can be other configurations. For example, the delivery port 44 can be a slit orifice, such as that disclosed in U.S. application Ser. No. 09/045,944, the entire disclosure of which is hereby incorporated herein by reference, or a spiral orifice, such as that disclosed in U.S. application Ser. No. 08/595,761, the entire disclosure of which is hereby incorporated herein by reference.

The dimensions of the port 44 in terms of both diameter and length will vary with the type of beneficial agent 24, the rate at which the beneficial agent is to be delivered, and the environment into which it is to be delivered. The considerations involved in determining the optimum dimensions of the delivery port 44 for any particular enclosure or beneficial agent 24 are the same as those for delivery ports or orifices of enclosures of the prior art, and selection of the appropriate dimensions will be readily apparent to those skilled in the art.

The capsule 22 is formed of a material that is sufficiently rigid to withstand expansion of an osmotic agent 26 without changing size or shape. The capsule 22 is preferably substantially impermeable to fluids in the environment as well as to ingredients contained within the osmotic delivery system 20 such that the migration of such materials into or out of the capsule through the impermeable material of the capsule is so low as to have substantially no adverse impact on the function of the osmotic delivery system 20.

Materials that can be used for the capsule 22 are preferably sufficiently strong to ensure that the capsule will not leak, crack, break, or distort under stresses to which it would be subjected during implantation or under stresses due to the pressures generated during operation of the osmotic delivery system 20.

The capsule 22 can be formed of chemically inert and biocompatible, natural or synthetic materials that are known in the art. The capsule material is preferably a non-bioerodible material that can remain in a patient after use, such as titanium or a titanium alloy, and is largely impermeable to materials within and outside the capsule 22. However, the material of the capsule 22 can alternatively be a bioerodible material that bioerodes in the environment after dispensing the beneficial agent. Generally, preferred materials for the capsule 22 are those acceptable for human implants.

In general, typical materials of construction suitable for the capsule 22 include non-reactive polymers or biocompatible metals or alloys. The polymers include acrylonitrile polymers such as acrylonitrile-butadiene-styrene terpolymer, and the like; halogenated polymers such as polytetrafluoroethylene, polychlorotrifluoroethylene, copolymer tetrafluoroethylene and hexafluoropropylene polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule 22 include stainless steel, titanium, platinum, tantalum, gold, and their alloys, as well as gold-plated ferrous alloys, platinum-plated ferrous alloys, cobalt-chromium alloys and titanium nitride coated stainless steel. The capsule 22 can be formed from any of the above-mentioned wall-forming materials by the use of a mold, with the materials applied either over the mold or inside the mold, depending on the mold configuration. Additionally, the capsule 22 can be formed by machining. Any of the wide variety of techniques known in the pharmaceutical industry can be used to form the capsule 22.

Figure 4:
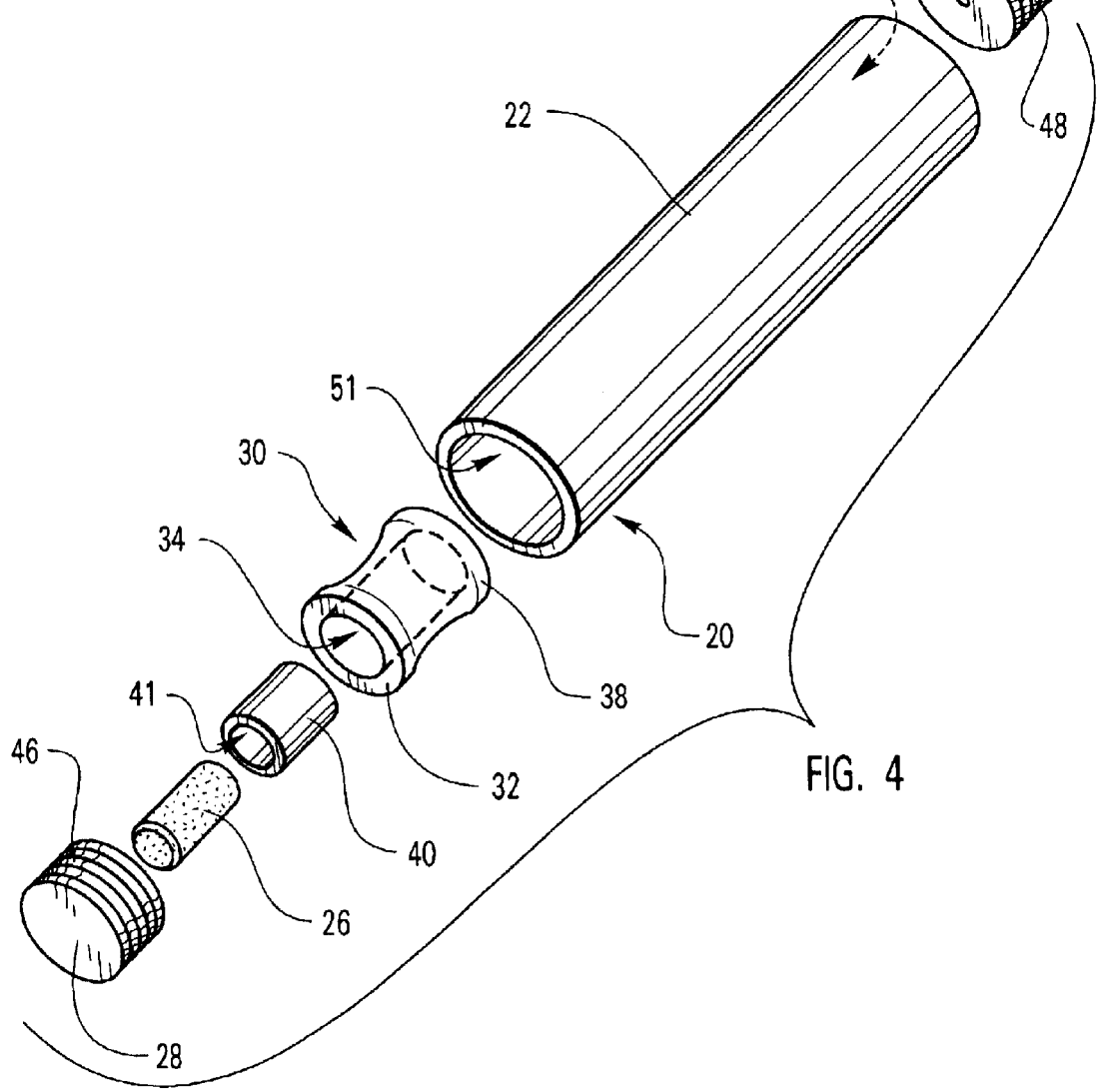
FIG. 4 is an exploded perspective view of an osmotic delivery system according to one embodiment of the present invention.

The interior of the capsule 22 receives the osmotic agent 26, which in the embodiment of the present invention depicted in FIGS. 1 and 4 is an osmotic tablet. The osmotic agent 26, specifically the osmotic tablet of the embodiment of the present invention illustrated in FIG. 1, drives the osmotic flow of the osmotic delivery system 20. The osmotic agent 26 need not be a tablet; it may be other conceivable shapes, textures, densities, and consistencies and still be within the confines of the present invention. Additionally, more than one osmotic tablet may be used to drive the osmotic flow of the osmotic delivery system 20. When the osmotic delivery system 20 is assembled, the capsule 22 contains the osmotic agent 26.

The osmotic agent 26 is a liquid-attracting agent used to drive the flow of the beneficial agent 24 from the osmotic delivery system 20. The osmotic agent 26 may be an osmagent, an osmopolymer, or a mixture of the two. Species that fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species that fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite® polyacrylic acids having molecular weights of 80,000 to 200,000, Polyox Polyethylene oxide polymers having molecular weights of 100,000 to 5,000,000, starch graft copolymers, and Aqua-Keeps acrylate polymer polysaccharides.

The osmotic agent 26 may be manufactured by a variety of techniques, many of which are known in the art. In one such technique, an osmotically active agent is prepared as solid or semi-solid formulations and pressed into pellets or tablets whose dimensions correspond to slightly less than the internal dimensions of the respective chambers which they will occupy in the capsule interior. Depending on the nature of the materials used, the agent and other solid ingredients that may be included, can be processed prior to the formation of the pellets by such procedures as ballmilling, calendaring, stirring or rollmilling to achieve a fine particle size and hence fairly uniform mixtures of each.

The beneficial agent 24 may optionally include pharmaceutically acceptable carriers and/or additional ingredients such as antioxidants, stabilizing agents, permeation enhancers, etc. In other embodiments of this invention, the beneficial agent 24 contained in the capsule 22 may include flowable compositions such as liquids, suspension, or slurries, which are typically poured into the capsule after the osmotic agent 26 and the body 32 of the piston 30 have been inserted in the capsule.

Patients to whom beneficial agents 24 may be administered using systems of this invention include humans and animals. The invention is of particular interest for applica tion to humans and household, sport, and farm animals, particularly mammals. For the administration of beneficial agents, the devices of the present invention may be implanted subcutaneously or intraperitoneally wherein aqueous body fluids or liquids are available to activate the osmotic agent 26. Devices of the invention may also be administered to the rumen of humans and ruminant animals, in which embodiment the devices may further comprise a conventional density element for maintaining the device in the rumen for extended periods of time of up to 120 days or longer.

The present invention applies to the administration of beneficial agents in general, which include any physiologically or pharmacologically active substance. The beneficial agent 24 may be any of the agents that are known to be delivered to the body of a human or an animal such as medicaments, vitamins, nutrients, or the like. The beneficial agent 24 may also be an agent that is delivered to other types of aqueous environments such as pools, tanks, reservoirs, and the like. Included among the types of agents that meet this. description are biocides, sterilization agents, nutrients, vitamins, food supplements, sex sterilants, fertility inhibitors and fertility promoters.

Drug agents that may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, antiinflammatory corticosteroids, ocular drugs and synthetic analogs of these species.

Examples of drugs that may be delivered by devices according to this invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofl urophate, acetazolamide, methazolamide, ebendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalaline, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives.

The beneficial agent 24 can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, acetate, sulfate, laurylate, oleate, and salicylate. For acidic compounds, salts of metals, amines or organic cations may be used. Derivatives such as esters, ethers and amides can also be used. A beneficial agent can be used alone or mixed with other agents.

Osmotic delivery systems according to the present invention are also useful in environments outside of physiological or aqueous environments. For example, the osmotic delivery system may be used in intravenous systems (attached to an IV pump or bag or to an IV bottle, for example) for delivering beneficial agents to an animal or human. Osmotic delivery systems according to the present invention may also be utilized in blood oxygenators, kidney dialysis and electrophoresis, for example. Additionally, devices or systems of the present invention may be used in the biotechnology area, such as to deliver nutrients or growth regulating compounds to cell cultures. In such instances, activating mechanisms such as mechanical mechanisms are particularly useful.

The osmotic delivery system 20 also includes the aforementioned semipermeable body 28, such as the semipermeable plug illustrated in FIGS. 1 and 4. The semipermeable body 28 is formed of a semipermeable material that allows liquid to pass from an exterior environment of use into the capsule 22 to cause the osmotic agent 26 to swell. But the material forming the semipermeable body 28 is largely impermeable to the materials within the enclosure and other ingredients within the environment of use. As illustrated in FIG. 1, the semipermeable body 28 is in the shape of a plug that is inserted into the first opening 51 of the capsule 22 at the first end 50. The semipermeable body 28 defines part of the enclosure 21 because it closes-off the first opening 51 of the capsule 22. Alternatively, the semipermeable body 28 may be located distant from the enclosure 21, but communicate liquid from a surrounding environment of use to the osmotic agent 26 through a tube in liquid communication with the capsule 22 or through other means for communicating liquid. The semipermeable body 28 may also be a membrane coating on the exterior surface of the capsule 22 or a sleeve or cap that slides over a portion of the capsule 22 to enclose the osmotic agent 26.

As shown in FIG. 1, the osmotic delivery system 20 includes the semipermeable body 28, such as the semipermeable plug illustrated. The semipermeable body 28 is typically cylindrically shaped, and has means for sealing or ribs 46 extending outwardly from the outer surface of the semipermeable body. The ribs 46 are the means by which the semipermeable plug operates like a cork or stopper, obstructing and plugging the opening 51 in the capsule 22 of the osmotic delivery system 20 illustrated in FIG. 1. The means for sealing 46 may be the exemplary ribs, or may be other configurations such as threads, a tight interference fit between an outer sealing surface of the plug and the capsule 22, glue, adhesives, ridges, lips, or other devices which join the semipermeable body 28 with the capsule 22 to prevent leakage. The semipermeable body 28 is, therefore, intended for at least partial insertion into an opening of the capsule 22, and the means for sealing 46 the environment of use from an inside of the capsule 22 prevents liquid and other substances in the environment of use, besides the permeation liquid, from entering the osmotic delivery system 20 while also preventing materials from the inside of the delivery system from leaking or escaping to the environment of use.

The semipermeable body 28 is made from a semipermeable material. The semipermeable material of the body 28 allows liquids, especially water, to pass from an exterior environment of use into the capsule 22 to cause the osmotic agent 26 to swell. However, the semipermeable material forming the semipermeable body 28 is largely impermeable to the materials within the capsule 22 and other ingredients within the fluid environment.

Semipermeable compositions suitable for the semipermeable body 28 are well known in the art, examples of which are disclosed in U.S. Pat. No. 4,874,388, the entire disclosure of which is incorporated herein by reference. Such possible semipermeable materials from which the body 28 can be made include, but are not limited to, for example, Hytrel polyester elastomers (DuPont), cellulose esters, cellulose ethers and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. By, "degree of substitution," or "D.S.," is meant the average number of hydroxyl groups originally present on the anhydroglucose unit comprising the cellulose polymer that is replaced by a substituting group. Representative materials include, but are not limited to, one selected from the group consisting of cellulose acylate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and acetyl content of 4 average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Other materials for the semipermeable body 28 are polyurethane, polyetherblockamide (PEBAX, commercially available from ELF ATOCHEM, Inc.), injection-moldable thermoplastic polymers with some hydrophilicity such as ethylene vinyl alcohol (EVA). The composition of the semipermeable body 28 is permeable to the passage of external liquids such as water and biological liquids, and it is substantially impermeable to the passage of beneficial agents, osmopolymers, osmagents, and the like.

The osmotic delivery system 20 also includes the movable space-efficient piston 30. The piston 30 is a member that is matingly received by the hollow interior of the capsule 22 and moves when subjected to pressure from the osmotic agent 26 to displace or move the beneficial agent 24. The piston 30 forms a movable seal with the interior surface of the capsule 22. The movable seal formed by the piston 30 separates the osmotic agent 26 and the beneficial agent 24 such that the osmotic agent 26 does not substantially leak or seep past the piston seal and adversely affect the function of the beneficial agent. Hence, the osmotic agent 26 is separated from the beneficial agent 24 by the movable piston 32.

As illustrated in FIG. 3, the body 32 of the piston 30 is a substantially cylindrical member that is configured to fit in the capsule 22 in a sealing manner that allows the piston to slide within the capsule in the longitudinal direction of the capsule. That is, the exterior surface of the piston body 32 abuts against and slides relative to the interior cylindrical surface of the capsule 22. Because the semipermeable body 28 is lodged within the first opening 51, the piston also moves relative to the semipermeable body 28.

The piston body 32 includes annular ring-shaped protrusions or ribs 38 that define the movable or sliding seal with the inner surface of the capsule 22. The ribs 38 are the most outwardly radial surface of the piston body 32. The ribs 38 are the means by which the piston 30 forms a seal with the interior surface of the capsule 22. Thus, the outermost radial diameter of the piston body 32 is greater than the inner diameter of the capsule 22. Although the piston body 32 illustrated in FIG. 3 includes two ribs, other pistons according to the present invention may include one or more ribs. Additionally, the piston body 32 need not include ribs. For example, the exterior surface of the piston body can be entirely cylindrical such that the entire cylindrical exterior surface of the piston body effects a seal with the interior surface of the capsule 22. However, the ribs 38 are preferred as they effect a better movable seal with the interior surface of the capsule 22, as compared to a piston body having an exterior surface that is entirely cylindrical. The piston body 32 is preferably formed of an impermeable resilient and inert material. In general, materials suitable for the piston body 32 are elastomeric materials including the non-reactive polymers listed above in reference to the materials for the capsule 22, as well as elastomers in general, such as polyurethanes and polyamides, chlorinated rubbers, styrene-butadiene rubbers, and chloroprene rubbers.

As illustrated in FIG. 3, the piston body 32 includes a hollow interior portion or recess 34, such as the cylindrical cavity illustrated. The recess 34 can be other configurations such as a square cavity, concave indentation, conical pit, cup, gouge, depression, or similar space adapted to receive the osmotic agent 26. The recess 34 has a cylindrical and longitudinal interior surface 33 that begins at an insert opening 31 formed by the recess 34 in the first end 35 of the piston body 32, and ends at a depth surface 36 within the body 32 close to the second end 37 of the body 32. Because of the general cylindrical shape of the outer surface of the piston body 32 and the cylindrical shape of the recess 34, the piston is thimble or cup-shaped such that a "bottom of the cup" has a thickness. Because the piston 30 separates the beneficial agent 24 and the osmotic agent 26, the recess 34 preferably does not pierce completely through the piston body 32. The piston body 32 is cup-shaped because the recess 34 defines a hollow area within the piston body 32.

The longitudinal axis of the recess 34 is approximately parallel to the longitudinal axis of the capsule 22, and is preferably coincident with the longitudinal axis of the capsule 22. Additionally, the opening 31 of the recess 34 faces away from the delivery port 44, i.e., toward the semipermeable body 28. The depth surface 36 of the recess preferably extends past the median of the piston body 32 along the longitudinal axis of the piston as measured from the first end 35. The diameter of the recess 34 is typically 50%, preferably greater than 60%, and preferably less than 80% of the inner diameter of the capsule 22. By increasing the diameter of the recess 34, the wall thickness of the piston body 32 decreases. It is preferable that the recess 34 occupy as much internal volume of the piston 30 as possible without destroying the effectiveness of the piston seal when the piston 30 is inserted into the capsule 22. Additionally, the exterior surface of the piston body 32 can take other shapes, such as a chevron or cantilever shape.

Although the cylindrical configuration of the recess 34 is preferred, other configuration recesses fall within the confines of the present invention. For example, the recess 34 or hollow interior portion may be square, rectangular, octagonal, triangular, oval, half-circular, circular, or a shape that matches the shape of the exterior surface of the piston body 32. Likewise, the hollow interior portion 34 may be a series or plurality of recesses, tubes, slots, or gaps within the interior of the piston body 32. All of the above, and other configurations, would function to receive a portion of the osmotic agent 26 such that the piston 30 occupies less space within the capsule 22.

The recess 34 of the piston body 32 receives the osmotic agent 26, such as the osmotic tablet illustrated in FIG. 1. Additionally, the recess 34 also matingly receives an insert or sleeve 40, such as the cylindrical tube illustrated in FIGS. 1 and 2. The sleeve 40 is preferably made from a rigid and impermeable material such as that used for the capsule 22, and helps effect a movable seal between the piston and the interior surface of the capsule 22. For example, the sleeve 40 can be formed from polycarbonate, polysulfone, polystyrene, or an acetal such as DELRIN®(DuPont). The sleeve 40 also can be made out of an inert metal such as stainless steel or titanium. The sleeve 40 is inserted into the recess 34 and has an outer diameter that at least matches the diameter of the recess 34. Because the recess 34 receives the sleeve 40, it is preferable that the shape of the exterior surface of the sleeve 40 matches or corresponds to the shape of the recess 34. For example, the recess 34 and the sleeve 40 are both cylindrical. It is also preferable that the wall-thickness of the sleeve 40 be thin so as to occupy little space within the recess 34. In general, the wall-thickness of the sleeve 40 must be thick enough to impart enough rigidity to the sleeve to maintain the piston seal with the interior surface of the capsule 22.

The sleeve 40 is sized such that the recess 34 matingly receives the sleeve 40. In instances where it is desirable to increase the outer diameter of the piston body 32, if the piston body 32 is formed of a resilient material, the outer diameter of the sleeve 40 may be greater than the diameter of the recess 34 such that the piston body 32 deflects radially and outwardly when the sleeve 40 is inserted therein. In the embodiment illustrated in FIG. 1, the longitudinal length of the sleeve 40 is substantially equal to the longitudinal depth of the recess 34 in the piston body 32.

It will be appreciated that the sleeve 40 may be in any number of different shapes and sizes, but preferably matches the shape and size of the recess 34 into which the sleeve 40 is inserted. For example, the sleeve 40 may be cup-shaped or shaped like a chevron. In general, the sleeve 40 stabilizes the dimensions and sealing forces of the piston body 32 as the piston moves, especially if an osmotic tablet is used that dissolves into a fluid during operation of the osmotic delivery system 20. Additionally, the sleeve 40 helps prevent the beneficial agent 24 from diffusing into the osmotic agent 26 during storage of the osmotic delivery device 20.

The sleeve 40 is preferably inserted into the recess 34 for assisting the piston body 32 in effecting a movable seal with the interior surface of the capsule 22. Because the piston body 32 is preferably flexible and resilient, the wall of the piston body 32 flexes toward the interior of the recess 32 after the piston body 32 is inserted into the capsule 22. By inserting the preferably rigid sleeve 40 into the opening 31 of the recess 34 such that the sleeve 40 is matingly received, the wall of the piston body 32 will not overly flex inwardly toward the recess 34, and the seal formed between the outer surface of the piston 30 and the interior surface of the capsule 22 is maintained.

Figure 6:
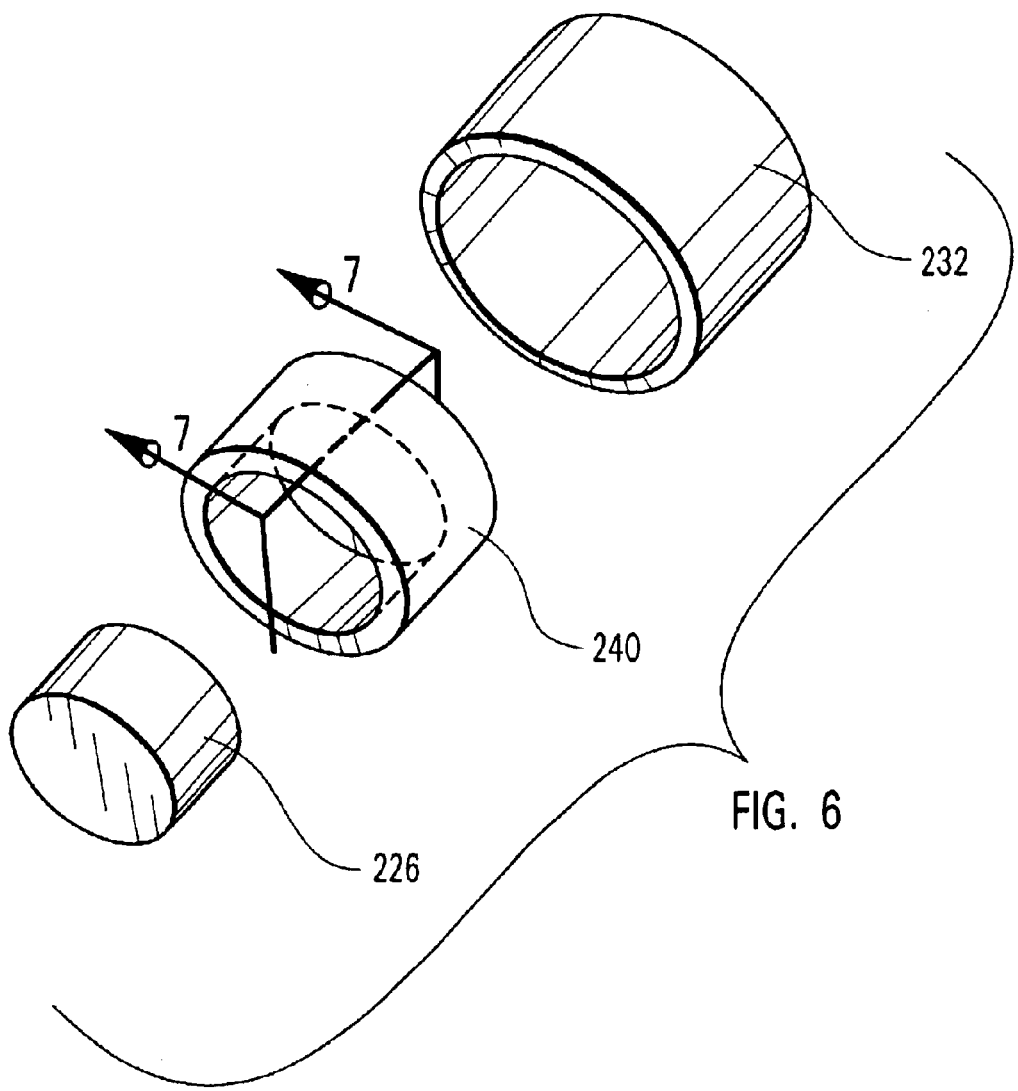
FIG. 6 is a perspective view of a cup-shaped sleeve for insertion into a recess of a piston in accordance with another embodiment of the present invention.
Figure 7:
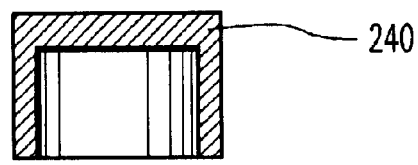
FIG. 7 is sectional view of the sleeve of FIG. 6 taken along the line 7—7 of FIG. 6.

FIGS. 6 and 7 illustrate another embodiment of a sleeve. As shown by FIGS. 6 and 7, the sleeve 240 is in the shape of cup, such as a cap or thimble. The sleeve 240 is inserted into the piston 232, and the osmotic agent 226 is inserted in the recess formed by the cup-shaped sleeve 240. The sleeve 240 may be fabricated from an inert and rigid material to ensure that the piston is impermeable.

Although the piston 30 illustrated in FIG. 1 includes the sleeve 40, in some instances, it may not be necessary to include the sleeve 40 in the recess 34 as the material of the piston body 32 is sufficiently rigid to effect a satisfactory seal between the interior surface of the capsule 22 and the piston body 32. In this case, the sleeve 40 need not be inserted into the recess 34. Generally, the wall thickness and the structural characteristics of the piston body 32 determine whether or not a rigid sleeve 40 is needed to assist in defining the seal, which is determinable by experimental methods.

Figure 5:
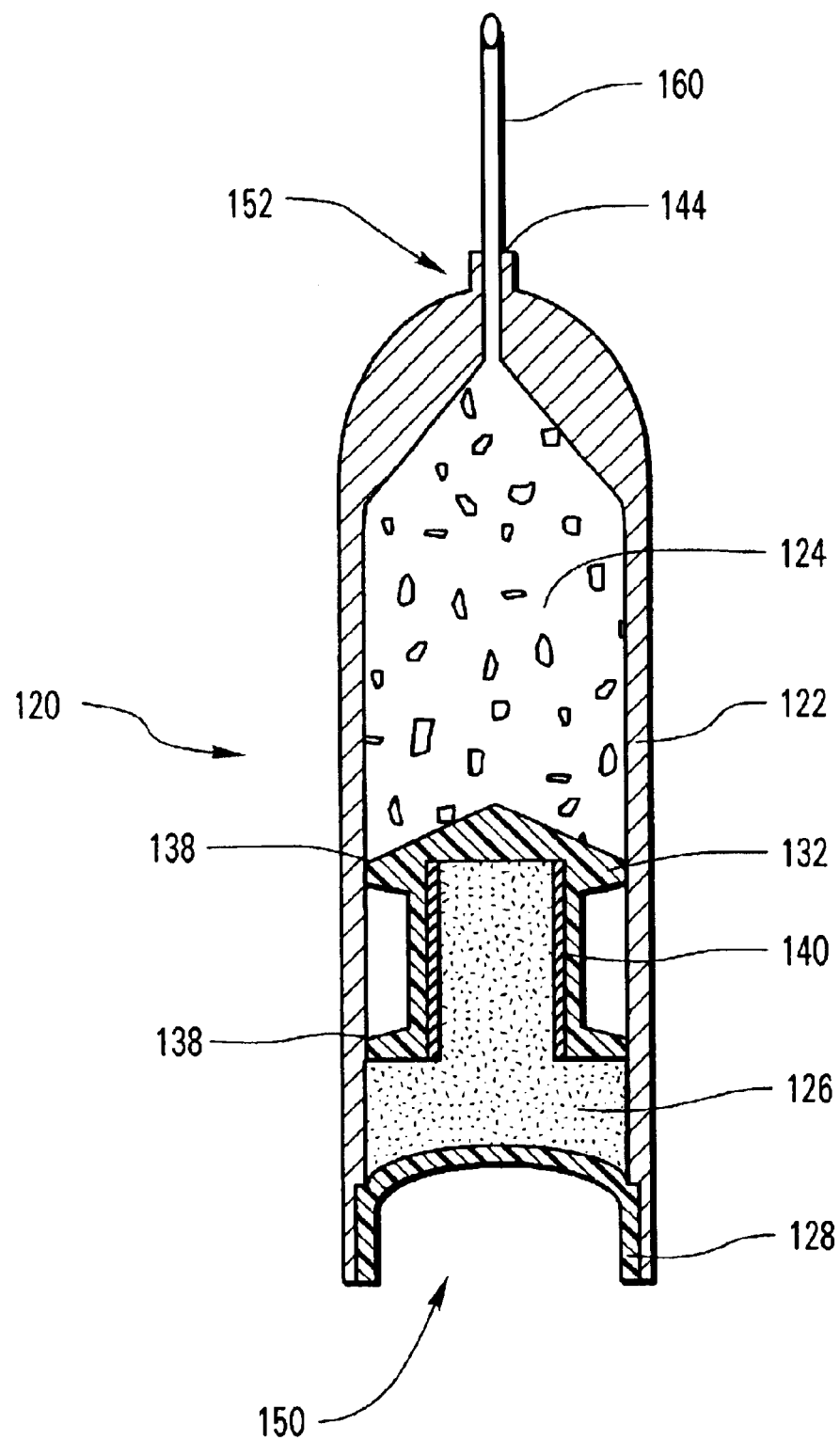
FIG. 5 is a sectional view of another osmotic delivery system according to the present invention.

The osmotic agent 26 is at least partially located within the recess 34. Preferably, the majority of the total weight of the osmotic agent 26 is located within the recess 34. The osmotic agent 26 may be completely located within the recess 34, or may extend partially from the recess 34. As illustrated in FIG. 1, the volume of the osmotic agent 26 is greater than that of the recess 34 such that the osmotic agent extends from the recess 34 and into a gap or space 54 located between the piston 30 and the semipermeable body 28. The osmotic agent 26 may completely fill the gap 54 such as shown in FIG. 5, or only partially fill the gap 54, as shown in FIG. 1.

The piston body 32 is preferably injection molded. However, the piston body 32 may be fashioned by a different process. For example, the piston body 32 may also be made from extrusion, reaction injection molding, rotational molding, thernoforming, compression molding, and other known processes. If an injection molding process is used to form the piston body 32, the ejector pin or core may be used to form the recess 34, and different length and sized ejector pins or cores may be easily changed to fashion different size recesses 34 to controllably vary the amount of osmotic agent that is received by the recess 34 of the piston 30. Additionally, the recess 34 may be formed in the piston body 32 after the piston body has been formed without a recess. For example, a cylinder of material may be fabricated and sliced into smaller cylinders. Thereafter, a cylindrical section may be removed from the piston body to form the recess 34 in the piston body 32.

Furthermore, the piston body 32 need not be the unitary structure illustrated in FIG. 3. A cylindrical tube may be attached to a flat circular disk to define the cup-shape of the piston 30. Additionally, the sleeve 40 may be cup-shaped, and a resilient tube with ribs may wrap around an outer cylindrical surface of the sleeve to define the piston 30.

It is preferable that the piston body 32 be substantially impervious to liquids, such that the osmotic agent and the liquid that permeates through the semipermeable body 28 does not diffuse through the piston body 32 and affect the beneficial agent 24 located on the side of the piston 30 opposite from that of the osmotic agent 26, and such that the beneficial agent does not diffuse through the piston body 32 and affect the performance of the osmotic agent 26.

Because the recess 34 of the piston body 32 at least receives a portion of the osmotic agent 26, the total volume of the osmotic delivery system 20, as compared to past systems, may be efficiently utilized. That is, rather than locating the osmotic agent 26 entirely between a semipermeable body and a known piston having no recess, the osmotic agent is at least partially located within the piston such that the space within the capsule 22 is efficiently utilized. The space-efficient piston 30 occupies less space in the capsule 22 of the osmotic delivery system 20, as compared to conventional pistons. Because the piston 30 occupies less space within the capsule 22, the internal volume of the interior of the capsule 22 need not be overly increased, if increased at all, to accommodate for the extra space occupied by the piston such that the amount of osmotic agent or beneficial agent in the capsule does not excessively vary when the piston 30 is used. This characteristic of the osmotic delivery system 20 increases the amount of time over which steady-state release of the beneficial agent 24 may be obtained as compared to past osmotic delivery systems that include conventional pistons. Additionally, because the piston 30 occupies less volume than past pistons, the total internal volume of the capsule 22 of the osmotic delivery system 20 can be decreased to provide an enclosure that is more suitable for human or animal implantation.

The piston 30 can also be used with existing osmotic delivery systems that utilize conventional pistons to increase the duration of continuous or pulsatile delivery of a beneficial agent from the osmotic delivery system. This is because the recess 34 can receive additional osmotic agent or because the existing osmotic agent can be located within the recess 34 so that the delivery system can hold additional beneficial agents. The factors that determine how much osmotic agent is needed to obtain sustained release of beneficial agents from osmotic delivery systems are described in a publication by F. Theeuwes and S. I. Yum, *Principles of the Design and Operation of Generic Osmotic Pumpsfor the Delivery of Semisolid or Liquid Drug Formulations*, ANNALS OF BIOMEDICAL ENGINEERING 41,1976, at 343–353, the entire disclosure of which is hereby incorporated herein by reference.

In assembling the osmotic delivery system 20 according to one embodiment of the present invention, the sleeve 40 is first inserted into the recess 34 of the piston 30. Then, the piston 30 is inserted into the first opening 51 of the capsule 22. Once the osmotic agent pellet or tablet has been formed, it is placed inside the recess 34 such that the hollow interior 41 of the sleeve 40 receives the osmotic agent 26. If the osmotic agent is a powder formulation, it can be poured into the recess 34. After the osmotic agent is located within the capsule 22, the semipermeable body 28 is inserted into the first opening to close-off the first end 50 of the enclosure 21. At this stage of the assembly process, the osmotic agent 26 is located between the semipermeable body 28 and the piston body 32. The beneficial agent 24 is then inserted into the second opening 53 of the capsule 22 such that the beneficial agent is directly adjacent to the piston 30. Thereafter, the plug-like member 42 having means for sealing or ribs 48 extending outwardly from the outer surface thereof is inserted into the second opening to close-off the second end of the enclosure 21 and complete the osmotic delivery system 20.

FIG. 5 illustrates an alternative embodiment of an osmotic delivery system 120 according to the present invention. The foregoing and following discussion of the benefits and function of the osmotic delivery system 20 also applies to the osmotic delivery system 120. Thus, the osmotic delivery system illustrated in FIG. 4 has been assigned corresponding reference numbers as the osmotic delivery system 20, increased by 100. The osmotic delivery system 120 illustrated in FIG. 4 also includes many additional features and inherent functions as described further below.

As illustrated in FIG. 5, the osmotic delivery system 120 includes an elongated substantially cylindrical capsule 122 having an opening through which a semipermeable body 128 has been inserted. The semipermeable body 128 is a cup-shaped membrane that has been inserted into an opening in the first end 150 of the capsule 122.

Also located within the capsule 122 is the osmotic agent 126, which is a powder formulation. The osmotic agent 126 is received by the recess of the piston body 132, as is the sleeve 140. Because the osmotic agent 126. is a powder formulation, it generally occupies the entire space or gap between the piston body 132 and the semipermeable body 128. Thus, the powder formulation of the osmotic agent efficiently utilizes the space between the piston body 132 and the semipermeable body 128.

The capsule 122 of the osmotic delivery system 120 defines a delivery port 144 at the second end 152. Attached to the delivery port 144 is a catheter or tube 160 that delivers the beneficial agent dispensed from the capsule 122 to a remote location. Hence, the osmotic delivery system 120 does not include a plug-like member having a delivery port such as the plug-like member 42 shown in FIG. 1. Protrusions or ribs 138 of the piston body 132 seal the beneficial agent 124 from the osmotic agent 126.

While the invention has been described in detail with reference to a preferred embodiment thereof, it will be apparent to one skilled in the art that various changes can be made, and equivalents can be employed without departing from the spirit and scope of the invention.

We claim:

1. An osmotic delivery system comprising:
   an enclosure, said enclosure having an interior for holding a beneficial agent, said interior having an interior surface;
   an osmotic agent located in said interior;
   a semipermeable body in liquid communication with said enclosure for permitting liquid to permeate through said semipermeable body to said osmotic agent; and
   a piston located within said interior of said enclosure, being movable with respect to said interior of said enclosure, defining a movable seal with said interior of said enclosure that separates said osmotic agent from said beneficial agent, and having a recess that receives a sleeve having an interior that receives at least a portion of said osmotic agent, said osmotic agent located between said piston and said semipermeable body, said osmotic agent for imbibing liquid from a surrounding environment through said semipermeable body to cause said piston to move and in turn cause delivery of said beneficial agent from said enclosure, wherein said osmotic agent consists of a semisolid or a solid.

2. The osmotic delivery system according to claim 1, wherein said osmotic agent is in the form of a tablet, pellet, or powder at least partially within said recess.

3. The osmotic delivery system according to claim 1, wherein said interior of said enclosure includes said interior surface, said piston abutting against said interior surface.

4. The osmotic delivery system according to claim 1, wherein said semipermeable body is located at least partially within said interior of said enclosure.

5. The osmotic delivery system according to claim 1, wherein said enclosure includes an opening and said semipermeable body includes a semipermeable plug, said semipermeable plug located at least partially within said opening.

6. The osmotic delivery system according to claim 1, wherein said enclosure includes an opening and said semipermeable body includes a semipermeable membrane, said semipermeable membrane located at least partially within said opening.

7. The osmotic delivery system according to claim 1, wherein said enclosure is a capsule.

8. The osmotic delivery system according to claim 1, wherein said enclosure includes a cylindrical tube.

9. The osmotic delivery system according to claim 1, wherein said osmotic agent is located between said semipermeable body and said piston.

10. The osmotic delivery system according to claim 1, wherein a portion of said osmotic agent is located outside of said recess.

11. The osmotic delivery system according to claim 1, wherein said piston is cup-shaped.

12. The osmotic delivery system according to claim 1, wherein said recess is cylindrical.

13. The osmotic delivery system according to claim 1, wherein said recess is a square cavity, concave indentation, conical pit, gouge, or depression.

14. The osmotic delivery system according to claim 1, wherein said piston includes at least one rib for effecting a movable seal with said enclosure.

15. The osmotic delivery system according to claim 1, wherein said piston includes a plurality of ribs for effecting said movable seal with said interior.

16. The osmotic delivery system according to claim 1, wherein said sleeve is cup-shaped.

17. The osmotic delivery system according to claim 1, wherein said beneficial agent is located in said interior of said enclosure, said beneficial agent being delivered from said enclosure when said piston moves.

18. The osmotic delivery system according to claim 1, wherein said beneficial agent is located in said interior of said enclosure, said piston defining said movable seal that separates said osmotic agent from said beneficial agent.

19. The osmotic delivery system according to claim 1, further comprising: an opening in said enclosure; and a plug located in said opening, said plug having a delivery port for delivery of said beneficial agent from the interior of said capsule.

20. The delivery system according to claim 1, further comprising: a delivery port in said enclosure for delivery of said beneficial agent from the interior of a capsule.

21. The osmotic delivery system according to claim 1, wherein said osmotic agent comprises an osmagent or an osmopolymer.

22. The osmotic delivery system according to claim 1, wherein said osmotic agent is magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, sucrose, glucose, lactose, fructose, dextran, poly(hydroxy-alkyl methacrylates) with molecular weight of about 30,000 to about 5,000,000, poly (vinylpyrrolidone) with molecular weight of about 10,000 to about 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of about 200 to about 30,000, a mixture of methyl cellulose, cross-linked agar and carboxymethylcellulose, a mixture of hydroxypropyl methylcellulose and sodium carboxymethylcellulose, a polymer of N-vinyllactams, polyoxyethylene-polyoxypropylene gels, a polyoxybutylene-polyethylene block copolymer gel, carob gum, polyacrylic gel, polyester gel, polyurea gel, polyether gel, polyamide gel, polypeptide gel, polyamino acid gel, polycellulosic gel, carbopol acidic carboxy polymer having a nolecular weight of about 250,000 to about 4,000,000, Cyanamer polyacrylamide, cross-linked indene-maleic anhydride polymer, polyacrylic acid having a molecular weight of about 80,000 to about 200,000, Polyox Polyethylene oxide polymer having a molecular weight of about 100,000 to about 5,000,000, starch graft copolymer, or an acrylate polymer polysaccharide.

* * * * *